United States Patent [19]

Pallos

[11] 4,130,662
[45] Dec. 19, 1978

[54] ACYLFORMANIDINE INSECTICIDAL AND MITICIDAL COMPOUNDS

[75] Inventor: Ferenc M. Pallos, Walnut Creek, Calif.

[73] Assignee: Stauffer Chemical Company, Westport, Conn.

[21] Appl. No.: 834,256

[22] Filed: Sep. 12, 1977

Related U.S. Application Data

[62] Division of Ser. No. 666,520, Mar. 12, 1976, Pat. No. 4,056,570, which is a division of Ser. No. 575,313, May 7, 1975, Pat. No. 3,962,305, which is a division of Ser. No. 439,507, Feb. 4, 1974, abandoned.

[51] Int. Cl.² ........................ A01N 9/20; A01N 9/24
[52] U.S. Cl. .................................................... 424/324
[58] Field of Search .............................. 424/326, 324

[56] References Cited

U.S. PATENT DOCUMENTS

| | | | |
|---|---|---|---|
| 3,502,720 | 3/1970 | Arndt et al. | 260/564 |
| 3,911,010 | 10/1975 | Wollweber et al. | 260/562 B |
| 3,960,947 | 6/1976 | Duerr et al. | 260/562 B |
| 4,056,570 | 11/1977 | Pallos | 424/326 |
| 4,071,556 | 1/1978 | Pallos | 424/326 |

FOREIGN PATENT DOCUMENTS 2202034  7/1972  Fed. Rep. of Germany.

*Primary Examiner*—Jerome D. Goldberg
*Assistant Examiner*—D. W. Robinson
*Attorney, Agent, or Firm*—Michael J. Bradley

[57] ABSTRACT

A composition of matter is described herein which has insecticidal and miticidal activity and methods of use. The composition may be defined by the following generic formula:

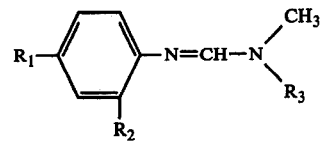

wherein $R_1$ and $R_2$ are independently methyl or halogen; $R_3$ is selected from the following groups:

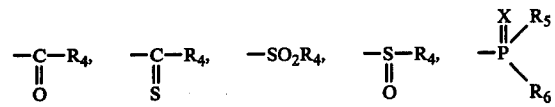

$R_4$ is selected from the group consisting of: alkyl, alkenyl, haloalkyl, haloalkenyl, cycloalkyl, cycloalkylalkyl, alkoxy, alkylthio, alkylamido, arylamido, alkoxyalkyl, alkylthioalkyl, alkylamidoalkyl, arylamidoalkyl, ketoalkyl, alkoxycarbonyl, alkoxycarbonylalkyl, alkylthiocarbonyl, alkylthiocarbonylalkyl, alkylamidocarbonyl, alkylamidocarbonylalkyl, arylamidocarbonylalkyl, hydroxyalkyl, N-alkylcarbamoylalkyl, N-arylcarbamoylalkyl, cyanoalkyl, thiocyanoalkyl, isothiocyanoalkyl, cyanatoalkyl, phenyl, furyl, thienyl, pyridyl with or without substituents, wherein said substituents can be selected from halogen, alkyl, haloalkyl, alkoxy, carbamyl, nitro, carboxylic acids and their esters, haloalkylcarbamyl; phenylalkyl; phenylhaloalkyl; phenylalkenyl; substituted phenylalkenyl wherein said substituents can be selected from halogen, alkyl, alkoxy; halophenoxy; phenylalkoxy, phenylalkylcarboxyalkyl; phenylcycloalkyl; halophenylalkenoxy; bicycloalkyl; with the proviso that when $R_4$ is alkoxycarbonyl, alkylthiocarbonyl or alkylamidocarbonyl $R_3$ can only be

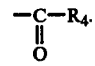

X = oxygen or sulfur $R_5$ and $R_6$ are independently alkyl, haloalkyl, aryl, alkoxy, aryloxy, alkylthio, arylthio, alkylamido and arylamido.

6 Claims, No Drawings

ACYLFORMANIDINE INSECTICIDAL AND MITICIDAL COMPOUNDS

This is a division of application Ser. No. 666,520 filed Mar. 12, 1976, now U.S. Pat. No. 4,056,570, which is a division of application Ser. No. 575,313, filed May 7, 1975, now U.S. Pat. No. 3,962,305, which is a division of application Ser. No. 439,507 filed Feb. 4, 1974, now abandoned.

BACKGROUND OF THE INVENTION

Among the many insecticidal and miticidal compounds available, various substituted formamidine compounds have shown such insecticidal and miticidal activity. Specific examples thereof and methods of use are those described in U.S. Pat. No. 3,502,720 and 3,378,437.

BRIEF DESCRIPTION OF THE INVENTION

It has been discovered that certain acylformamidine compounds are useful as insecticidal and miticidal compounds. These acylformamidine compounds may be defined by the following generic formula:

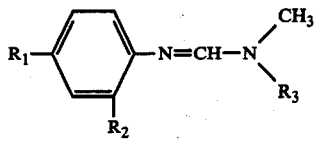

wherein $R_1$ and $R_2$ are independently methyl or halogen; $R_3$ is selected from the following groups:

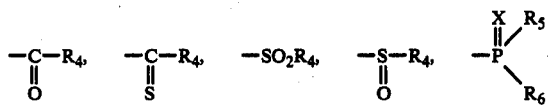

$R_4$ is selected from the group consisting of alkyl, alkenyl, haloalkyl, haloalkenyl, cycloalkyl, cycloalkylalkyl, alkoxy, alkylthio, alkylamido, arylamido, alkoxycarbonyl, alkoxycarbonylalkyl, alkylthiocarbonyl, alkylthiocarbonylalkyl, alkylamidocarbonyl, alkylamidocarbonylalkyl, arylamidocarbonylalkyl, alkoxyalkyl, alkylthioalkyl, alkylamidoalkyl, arylamidoalkyl, ketoalkyl, hydroxyalkyl, N-alkylcarbamoylalkyl, N-arylcarbamoylalkyl, cyanoalkyl, thiocyanoalkyl, isothiocyanoalkyl, cyanatoalkyl, phenyl, furyl, thienyl, pyridyl, with or without substituents, wherein said substituents can be selected from halogen, alkyl, haloalkyl, alkoxy, carbamyl, nitro, carboxylic acids and their esters, haloalkylcarbamyl; phenylalkyl; phenylhaloalkyl; phenylalkenyl; substituted phenylalkenyl wherein said substituents can be selected from halogen, alkyl, alkoxy, halophenoxy; phenylalkoxy, phenylalkylcarboxyalkyl; phenylcycloalkyl; halophenylalkenoxy; bicycloalkyl; with the proviso that when $K_4$ is alkoxycarbonyl, alkylthiocarbonyl or alkylamidocarbonyl, $R_3$ can only be

X = oxygen or sulfur; $R_5$ and $R_6$ are independently alkyl, haloalkyl, aryl, alkoxy, aryloxy, alkylthio, arylthio, alkylamido, arylamido.

DETAILED DESCRIPTION OF THE INVENTION

In the practice of the present invention, the compounds of the present invention are manufactured by reacting the properly selected 2, 4 disubstituted aniline with an alkyl orthoformate and then reacting the resulting alkylformimidate with methyl amine to obtain the 1 methyl 3 disubstituted phenyl formamidine which in turn is reacted with an acylating agent such as an acyl halide, an acyl anhydride or an isocyanate to produce the desired acylformamidine as is shown in the examples herein.

After the compounds of the present invention are formed, they can be applied to the habitat in an effective amount to control respective mites and insects.

The following examples illustrate the merits of the present invention

EXAMPLE 1

1-(2'-methyl-4'-chlorophenyl)-3-methyl-3-methylthiolcarbonylformamidine

Into a round-bottom flask, fitted with a mechanical stirrer, was placed 1.8 g (0.01 mole) 1-(2'-methyl-4'-chlorophenyl)-3-methylformamidine, 25 ml $CH_2Cl_2$ and 1.0 g (0.01 mole) triethylamine. The mixture was then cooled in an ice water bath. 1.1 g (0.01 mole) methyl chloro thioformate in 10 ml $CH_2Cl_2$ were slowly added dropwise and the mixture stirred at room temperature for one hour. The reaction mixture was washed twice with water, dried over magnesium sulfate, filtered and stripped. Product yield was 2.4 g of an oil ($N_D^{30}$ 1.5960). Structure was confirmed by N.M.R.

EXAMPLE 2

1-(2'-methyl-4'-chlorophenyl)-3-methyl-3 propionylformamidine

Into a round-bottom flask fitted with stirrer using the same procedure as Example 1, as added 1.8 g (0.01 mole) 1-(2'-methyl-4'-chlorophenyl)-3-methylformamidine, 25 ml $CH_2Cl_2$ and 1.0 g (0.01 mole) triethylamine. The mixture was cooled in an ice water bath and 0.92 g (0.01 mole) propionyl chloride in 10 ml $CH_2Cl_2$ was added slowly, dropwise. The remainder of the procedure is as in Example 1 above and yielded 1.7 g of solid product having a low melting point. Structure confirmation was by N.M.R.

EXAMPLE 3

1-(2'-methyl-4'-chlorophenyl)-3-methyl-3-methylcarboxyformamidine

Into a round-bottom flask fitted with stirrer were placed 1.8 g (0.01 mole) 1-(2'-methyl-4'-chlorophenyl)-3-methylformamide, 25 ml $CH_2Cl_2$ and 1.0 g triethylamine. The mixture was cooled in an ice-water bath and 0.94 g (0.01 mole) methyl chloroformate in 10 ml $CH_2Cl_2$ were added dropwise. The mixture was maintained and stirred at room temperature for one hour. The reaction mixture was washed twice with water and dried over magnesium sulfate ($MgSO_4$), filtered and stripped. The reaction yielded 1.7 g of an oil ($N_D^{30}$ 1.5622). Structure confirmation was by N.M.R.

EXAMPLE 4

1-(2'-methyl-4'-chlorophenyl)-3-methyl-3-i-butylthiocarbonylformamidine

Into a round-bottom flask fitted with a stirrer were added 1.8 g (0.01 mole) 1-(2'-methyl-4'-chlorophenyl)-3-methylformamidine, 25 ml $CH_2Cl_2$ and 1.0 g (0.01 mole) triethylamine. The mixture was cooled in an ice-water bath and 1.52 g (0.01 mole) i-butylchlorothioformate in 10 ml $CH_2Cl_2$ was added dropwise. The mixture was held at room temperature and stirred for one hour. The reaction mixture was washed twice with water and dried over $MgSO_4$, filtered and stripped. The reaction yielded 2.9 g of an oil ($N_D^{30}$ 1.5638). Structure confirmation was by N.M.R.

EXAMPLE 5

1-(2'-methyl-4'-chlorophenyl)-3-methyl-3-methylsuccinylformamidine

Into a round-bottom flask fitted with stirrer was placed 1.8 g (0.01 mole) 1-(2'-methyl-4'-chlorophenyl)-3-methylformamidine, 25 ml $CH_2Cl_2$ and 1.0 g triethylamine. The mixture was cooled in an ice-water bath and 1.5 g (0.01 mole) 3-carboxymethyl propionyl chloride in 10 ml $CH_2Cl_2$ was added. The mixture was stirred at room temperature for one hour. The reaction mixture was washed twice with water and dried over $MgSO_4$, filtered and stripped. Product yield was 2.3 g of a semi-solid. Structure confirmation was by N.M.R.

EXAMPLE 6

1-(2'-methyl-4'-chlorophenyl)-3-methyl-3-methylthiocarbamyl formamidine

Into a round-bottom flask fitted with stirrer, was placed 1.8 g (0.01 mole) 1-(2'-methyl-4'-chlorophenyl)-3-methylformamidine, 25 ml benzene, 0.73 g (0.01 mole) methylisothiocyanate plus two drops of triethylamine. The mixture was refluxed for two hours, cooled and evaporated. The reaction yielded 2.5 g of a solid, melting at 68°–70° C. Structure confirmation was by N.M.R.

EXAMPLE 7

1-(2'-methyl-4'-chlorophenyl)-3-methyl-3-dichloroacetylformamidine

The procedure was the same as in Example 3 above, with the exception that 1.47 g (0.01 mole) dichloroacetyl chloride was used in place of the methylchloroformate. Product yield was 2.2 g of a semi-solid. Structure confirmation was by N.M.R.

EXAMPLE 8

1-(2'-methyl-4'-chlorophenyl)-3-methyl-3-methylacrylformamidine

Procedure was the same as in Example 3 above, with the exception that 1.04 g (0.01 mole) methacryl chloride was used in place of methylchloroformate. The reaction yielded 2.3 g of an oil ($N_D^{30}$ 1.5684). Structure confirmation was by N.M.R.

EXAMPLE 9

1-(2'-methyl-4'-chlorophenyl)-3-methyl-3-trifluoroacetyl formamidine 1.8 g (0.01 mole) 1-(2'-methyl-4'-chlorophenyl)-3-methylformamidine were dissolved in 15 ml $CH_2Cl_2$ and cooled in an ice-water bath. 2.1 g (0.01 mole) trifluoroaceticanhydride in 10 ml $CH_2Cl_2$ were slowly added dropwise to the flask, and stirred at room temperature for one hour. The reaction mixture was washed with 10% $NaHCO_3$, dried over $MgSO_4$, filtered and stripped. The reaction yielded 1.9 g of an oil ($N_D^{30}$ 1.5182). Structure confirmation was by N.M.R.

EXAMPLE 10

1-(2'methyl-4'-chlorophenyl)-3-methyl-3-phenylthiocarbamylformamidine

The procedure was the same as in Example 6 above, with the exception that 1.35 g (0.01 mole) phenylisothiocyanate was used in place of methyl isothiocyanate. The reaction yielded 3.1 g of a low-melting material. Structure confirmation was by N.M.R.

Other compounds can be prepared in an analogous manner starting with the appropriate materials as outlined above. Following is a table of compounds representative of those embodied in the present invention. Compound numbers have been assigned to them and are used for identification throughout the balance of this specification.

TABLE I $$R_1\text{-}\underset{R_2}{\underset{|}{\text{C}_6\text{H}_3}}\text{-N=CH-N}\underset{R_3}{\overset{CH_3}{<}}$$

| Compound Number | $R_1$ | $R_2$ | $R_3$ |
|---|---|---|---|
| 1 | Cl | $CH_3$ | $-\text{CCH}_2\text{CCH}_3$ (with two C=O) |
| 2 | Cl | $CH_3$ | $-\text{P}(=S)(OCH_3)(OCH_3)$ |
| 3 | Cl | $CH_3$ | $-\text{CCOC}_2\text{H}_5$ (with two C=O) |
| 4 | Cl | $CH_3$ | $-\text{CCH}_2\text{COC}_2\text{H}_5$ (with two C=O) |
| 5 | Cl | $CH_3$ | $-\text{P}(=O)(OCH_3)(SCH_3)$ |
| 6 | Cl | $CH_3$ | $-\text{COCH}_3$ |
| 7 | Cl | $CH_3$ | $-\text{CO-n-C}_4\text{H}_9$ |
| 8 | Cl | $CH_3$ | $-\text{CO-}C_6H_5$ |
| 9 | Cl | $CH_3$ | $-\text{CCH}_2\text{CH}_2\text{COCH}_3$ (with two C=O) |
| 10 | Cl | $CH_3$ | $-\text{CCH}_3$ (C=O) |
| 11 | Cl | $CH_3$ | $-\text{CH}$ (C=O) |
| 12 | Cl | $CH_3$ | $-\text{CSCH}_3$ (C=O) |
| 13 | Cl | $CH_3$ | $-\text{CSC}_2\text{H}_5$ (C=O) |
| 14 | Cl | $CH_3$ | $-\text{CS-n-C}_3\text{H}_7$ (C=O) |

TABLE I-continued

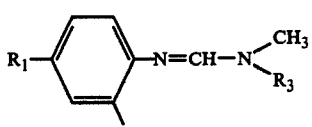

| Compound Number | $R_1$ | $R_2$ | $R_3$ |
|---|---|---|---|
| 15 | Cl | CH$_3$ | —C(=O)S-i-C$_3$H$_7$ |
| 16 | Cl | CH$_3$ | —C(=O)S-n-C$_4$H$_9$ |
| 17 | Cl | CH$_3$ | —C(=O)S-i-C$_4$H$_9$ |
| 18 | Cl | CH$_3$ | —C(=O)S-n-C$_8$H$_{17}$ |
| 19 | Cl | CH$_3$ | —C(=O)S—C$_6$H$_4$—Cl |
| 20 | Cl | CH$_3$ | —C(=O)SCH$_2$—C$_6$H$_5$ |
| 21 | Cl | CH$_3$ | —CC$_2$H$_5$ (C=O) |
| 22 | Cl | CH$_3$ | —C(=O)-n-C$_3$H$_7$ |
| 23 | Cl | CH$_3$ | —C(=O)-i-C$_3$H$_7$ |
| 24 | Cl | CH$_3$ | —C(=O)CHCl$_2$ |
| 25 | Cl | CH$_3$ | —C(=O)—C$_6$H$_5$ |
| 26 | Cl | CH$_3$ | —C(=O)CH=CH$_2$ |
| 27 | Cl | CH$_3$ | —C(OCH$_3$)=CH$_2$ |
| 28 | Cl | CH$_3$ | —SO$_2$CH$_3$ |
| 29 | Cl | CH$_3$ | —SO$_2$-i-C$_4$H$_9$ |
| 30 | Cl | CH$_3$ | —SO$_2$—C$_6$H$_4$—Cl |
| 31 | Cl | CH$_3$ | —COC$_2$H$_5$ (C=O) |
| 32 | Cl | CH$_3$ | —CO-n-C$_3$H$_7$ (C=O) |
| 33 | Cl | CH$_3$ | —CO-i-C$_4$H$_7$ (C=O) |
| 34 | Cl | CH$_3$ | —C(=O)NHCH$_3$ |
| 35 | Cl | CH$_3$ | —C(=O)NH—C$_6$H$_5$ |
| 36 | Cl | CH$_3$ | —C(=S)NHCH$_3$ |
| 37 | Cl | CH$_3$ | —C(=S)NH—C$_6$H$_5$ |
| 38 | Cl | CH$_3$ | —C(=O)OCH$_2$—C$_6$H$_5$ |
| 39 | Cl | CH$_3$ | —C(=O)CF$_3$ |
| 40 | Cl | CH$_3$ | —C(=O)CH$_2$Cl |
| 41 | Cl | CH$_3$ | —C(=O)CCl$_3$ |
| 42 | Cl | CH$_3$ | —C(=O)-t-C$_4$H$_9$ |
| 43 | Cl | CH$_3$ | —C(=O)NH-i-C$_3$H$_7$ |
| 44 | Cl | CH$_3$ | —C(=O)S-t-C$_4$H$_9$ |
| 45 | Cl | CH$_3$ | —C(=O)-sec-C$_4$H$_9$ |

Insecticidal activity of the above compounds were evaluated for efficacy on various insect species as follows:

I. Salt-marsh Caterpillar [*Estigmene acrea* (Drury)]

A. Leaf Dip Assay to Determine Efficacy Against First Instar Salt-Marsh Caterpillar Larvae Kidney bean leaves are dipped in a 50—50 acetone-water solution of the test chemical. When the leaves have dried, egg masses of the salt-marsh caterpillars are placed on the leaf surface. Mortality of the newly hatched larvae is determined after one week. Test concentrations range from 0.05% down to that at which approximately 50% of the larvae are dead.

B. Ovicidal Screening Procedure

Egg masses of the salt-marsh caterpillar are dipped in acetone solutions of the test chemicals and placed in petri dishes containing a portion of larval rearing medium. Efficacy is determined after seven days by observing the number of newly emerged larvae. Test concentrations range from 0.05% down to that at which approximately 50% of the eggs do not hatch.

II. Black Bean Aphid [*Aphis fabae* (Scop.)]

Nasturtium (Tropaeolum sp.) plants, approximately 2-3 inches tall, are transplated into sandy loam soil in 3-inch clay pots and infested with 50–75 aphids of mixed ages. Twenty-four hours later they are sprayed, to the point of runoff, with aqueous suspensions of the toxicant. The suspensions are prepared by diluting aliquots of the toxicant, dissolved in an appropriate solvent, with water to which has been added 0.0002% of a conventional wetting agent such as polyoxy-ethylene sorbitan monolaurate ether of alkylated phenol blended with organic sulfonate. Test concentrations ranged from 0.05% to that at which 50% mortality is obtained. Mortality is recorded after 48 hours and the LD-50 values are expressed as percent active ingredient in the aqueous suspensions.

III. Two-Spotted Mite [*Tetranychus urticae* (Koch)]

Pinto Beans (Phaseolus sp.) plants, approximately 2-3 inches tall, are transplanted into sandy loam soil in 3-inch clay pots and infested with 50-75 mites of mixed ages. Twenty-four hours later they are sprayed, to the point of runoff, with aqueous suspensions of the toxicant. The suspensions are prepared as in previously described tests (I and II). Test concentrations ranged from 0.05% to that at which 50% mortality is obtained. Mortality of adults, nymphs and eggs is recorded after 7 days and the LD-50 values are expressed as percent active ingredient in the aqueous suspensions.

IV. Systemic Tests

A. Salt-marsh Caterpillar:

Aliquots of toxicant dissolved in an appropriate solvent are diluted in water and placed in glass bottles. Concentrations of active ingredient range from 10 ppm to that at which 50% mortality is obtained. Kidney beans (*Phaseolus vulgaris*), supported by cotton plugs, are inserted into the solution so that the roots and major portion of the stem are completely immersed. Masses of caterpillar eggs which are nearly ready to hatch are fastened to the bean leaves. One week later mortality of the newly hatched larvae is recorded. LD-50 values are expressed as ppm of toxicant in the aqueous suspensions.

B. Two-Spotted Mite:

Preparation of the test solution and concentrations is the same as for the Salt-marsh Caterpillar test (IV-A). Pinto bean (Phaseolus sp.) plants with expanded primary leaves are placed in the solution so that the roots and major portions of the stem are completely immersed. immediately after, the leaves are infested with 75-100 mites of various ages. Mortality of adults, nymphs and eggs is recorded after one week, and LD-50 values are expressed as ppm of toxicant in the aqueous suspensions.

The results of the above test procedures indicate in Table II the effective concentration at which LD-50 control effect was achieved on the various species of insects.

TABLE II

| Compound Number | SMC | | | | 2SM | | |
|---|---|---|---|---|---|---|---|
| | BA % | Leaf Dip % | Ovicide % | SYS ppm | Pe % | Eggs % | SYS ppm |
| 1 | .03 | | .1 | 3 | .08 | .02 | >10 |
| 2 | .01 | | .01 | | .04 | .01 | |
| 3 | .005 | | .01 | .1 | .04 | .005 | 10 |
| 4 | .003 | | .005 | 3 | .04 | .006 | >10 |
| 5 | .01 | | >.1 | .5 | .08 | .02 | 10 |
| 6 | .05 | .0003 | .005 | 8 | >.05 | .05 | — |
| 7 | .001 | .0008 | .0008 | 1 | .03 | >.05 | >10 |
| 8 | .05 | .0005 | .008 | .2 | .005 | >.03 | >10 |
| 9 | .003 | .0003 | .008 | .5 | .01 | .03 | >10 |
| 10 | .001 | .0003 | .0008 | .3 | .01 | .03 | >10 |
| 11 | >.05 | .005 | >.05 | 3 | >.05 | >.05 | — |
| 12 | .003 | .001 | .03 | .3 | .005 | >.05 | >10 |
| 13 | .003 | .005 | .03 | .5 | .005 | >.05 | >10 |
| 14 | .0008 | .0003 | .003 | .1 | .008 | >.05 | >10 |
| 15 | .05 | .0005 | .005 | .3 | .01 | >.05 | >10 |
| 16 | .003 | .0008 | .005 | .3 | .01 | 22 .05 | >10 |
| 17 | .003 | .0008 | .005 | .08 | .03 | >.05 | >10 |
| 18 | .05 | .001 | .03 | 1 | .005 | .03 | >10 |
| 19 | .003 | .0005 | .03 | .3 | .03 | .03 | >10 |
| 20 | .001 | .0008 | .01 | .5 | .01 | .03 | >10 |
| 21 | >.05 | >.05 | >.05 | >10 | .05 | >.05 | — |
| 22 | >.05 | .03 | >.05 | >10 | >.05 | .05 | — |
| 23 | .003 | .003 | .03 | .3 | .01 | >.05 | 10 |
| 24 | .005 | .00008 | .01 | .3 | .01 | >.05 | >10 |
| 25 | >.05 | >.05 | >.05 | >10 | >.05 | >.05 | — |
| 26 | .03 | .008 | >.05 | 3 | .03 | >.05 | >10 |
| 27 | .003 | .0008 | .01 | .1 | .005 | >.05 | >10 |
| 28 | .05 | .0008 | >.05 | 3 | >.05 | >.05 | >10 |
| 29 | .005 | .008 | .03 | 3 | >.05 | >.05 | >10 |
| 30 | >.05 | .003 | >.05 | .8 | .03 | >.05 | >10 |
| 31 | .001 | .0008 | .03 | .3 | .01 | >.05 | >10 |
| 32 | .0008 | .01 | .003 | .8 | .03 | >.05 | >10 |
| 33 | .003 | .005 | .03 | >10 | .03 | >.05 | >10 |
| 34 | .05 | .05 | >.05 | 3 | >.05 | >.05 | >10 |
| 35 | .001 | .0003 | >.05 | .3 | .03 | .05 | >10 |
| 36 | .01 | .0005 | >.05 | .3 | .03 | >.05 | >10 |
| 37 | .003 | .00008 | .003 | .03 | .01 | >.05 | >10 |
| 38 | .005 | .0003 | .05 | .3 | .01 | .03 | |
| 39 | .003 | .0003 | .01 | .08 | .01 | >.05 | |
| 40 | >.05 | .0008 | >.05 | .3 | .03 | >.05 | |
| 41 | .01 | .00008 | .01 | .1 | .01 | >.05 | |
| 42 | .01 | .0008 | .05 | .08 | .01 | .03 | |
| 43 | >.05 | .0008 | >.05 | 5 | .03 | .03 | |
| 44 | .03 | .0001 | .008 | .8 | .03 | .05 | |

TABLE II-continued

| Compound Number | BA % | SMC Leaf Dip % | Ovicide % | SYS ppm | 2SM Pe % | Eggs % | SYS ppm |
|---|---|---|---|---|---|---|---|
| 45 | .03 | .001 | .03 | .8 | .01 | .03 | |

SMC = Salt-marsh Caterpillar
SYS = Systemic
2SM = Two-spotted Mite
BA = Bean Aphid
> = greater than
< = less than
Pe = Post-embryonic The compounds of this invention are generally embodied into a form suitable for convenient application. For example, the compounds can be embodied into pesticidal compositions which are provided in the form of emulsion, suspensions, solutions, dust and aerosol sprays. In general, such compositions will contain, in addition to the active compound, the adjuvants which are normally found in pesticide preparations. In these compositions, the active compounds of this invention can be employed as a sole pesticide component or they can be used in a mixture with other compounds having similar utility. The pesticide compositions of this invention can contain as adjuvants organic solvents such as sesame oil; xylene solvents; heavy petroleum, etc; water; emulsifying agents; surface active agents; talc; pyrophyllite; diatamite; gypsum; clays; propellents; such as dichlorodifluormethane; etc. If desired, however, the active compounds can be applied directly to feedstuffs, seeds, etc. upon which these pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served to the compound as rendered active by external influences, such as light or by some physiological action which occurs when the compound is ingested into the body of the pests.

The precise manner in which the pesticidal composition of this invention are used in any particular instance, will be readily apparent to a person skilled in the art. Generally, the active pesticide compound will be embodied in the form of a liquid composition. For example, an emulsion, suspension or aerosol spray. While the concentration of the active pesticide in the present compositions can vary within rather wide limits, ordinarily the pesticide compound will comprise not more than about 15.0% by weight of the pesticidal composition. Preferably, however, the pesticide compositions of this invention will be in the form of solutions or suspensions containing from about 0.1 to about 1.0% by weight of the active pesticide compound.

What is claimed is:

1. A method of controlling insects consisting of applying to said insects or the habitat thereof an insecticidally effective amount of a compound having the formula

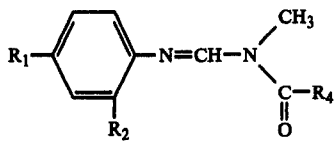

wherein $R_1$ and $R_2$ are independently methyl or halogen and $R_4$ is either haloalkyl or ketoalkyl.

2. The method as set forth in claim 1 wherein $R_1$ is Cl; $R_2$ is $CH_3$ and $R_4$ is

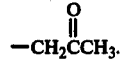

3. The method as set forth in claim 1 wherein $R_1$ is Cl; $R_2$ is $CH_3$ and $R_4$ is $-CHCl_2$.
4. The method as set forth in claim 1 wherein $R_1$ is Cl; $R_2$ is $CH_3$ and $R_4$ is $-CF_3$.
5. The method as set forth in claim 1 wherein $R_1$ is Cl; $R_2$ is $CH_3$ and $R_4$ is $-CH_2Cl$.
6. The method as set forth in claim 1 wherein $R_1$ is Cl; $R_2$ is $CH_3$ and $R_4$ is $-CCl_3$.

* * * * *